(12) United States Patent
Ker et al.

(10) Patent No.: US 10,978,902 B2
(45) Date of Patent: Apr. 13, 2021

(54) WIRELESS CHARGING DEVICE

(71) Applicant: NATIONAL CHIAO TUNG UNIVERSITY, Hsinchu (TW)

(72) Inventors: Ming-Dou Ker, Jhu-Bei (TW); Yu-Ting Cheng, Hsinchu (TW); Kuan-Jung Chen, Tainan (TW); Wei-Ming Chen, Hsinchu (TW); Chung-Yu Wu, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 217 days.

(21) Appl. No.: 16/360,346

(22) Filed: Mar. 21, 2019

(65) Prior Publication Data

US 2020/0212705 A1    Jul. 2, 2020

(30) Foreign Application Priority Data

Dec. 26, 2018    (TW) .................................. 107147273

(51) Int. Cl.
*H02J 7/02* (2016.01)
*H02J 7/00* (2006.01)
(Continued)

(52) U.S. Cl.
CPC .............. *H02J 7/025* (2013.01); *H01F 38/14* (2013.01); *H02J 7/0042* (2013.01); *H02J 50/10* (2016.02);
(Continued)

(58) Field of Classification Search
CPC ..................................................... H02J 7/025
(Continued)

(56) References Cited

U.S. PATENT DOCUMENTS

2018/0277296 A1* 9/2018 Endo ...................... H01F 41/046
2018/0286579 A1* 10/2018 Hanabusa ............... H01F 27/38

FOREIGN PATENT DOCUMENTS

KR    10-1570749 B1    11/2015
KR    10-1671329 B1    11/2016

OTHER PUBLICATIONS

Weiqing Zuo, Yang Yang, Xiaoxiang He, Dawei Zhan, Qifan Zhang, A Miniaturized Metamaterial Absorber for Ultrahigh-Frequency RFID System, IEEE Antennas and Wireless Propagation Letters, vol. 16, 2017, pp. 329-332.
(Continued)

*Primary Examiner* — Edward Tso
*Assistant Examiner* — Ahmed H Omar
(74) *Attorney, Agent, or Firm* — Rosenberg, Klein & Lee

(57) ABSTRACT

A wireless charging device includes a wireless charging transmitter transmitting a charging signal to a signal gain module to generate at least one gain signal. The signal gain module includes an insulation substrate with an upper surface thereof provided with a first conductive wire. The first conductive wire makes at least one turns arranged along the inner edge of the insulation substrate. The lower surface of the insulation substrate is provided with a second conductive wire whose position corresponds to the position of the first conductive wire. A connecting element is arranged between the first conductive wire and the second conductive wire, such that the first conductive wire is electrically connected to the second conductive wire through the connecting element. The present invention provides a charging signal with high intensity to avoid the low charging efficiency caused by deflection and too long a distance.

10 Claims, 6 Drawing Sheets

(51) Int. Cl.
  *H01F 38/14* (2006.01)
  *H02J 50/10* (2016.01)
  *A61N 1/36* (2006.01)
  *A61N 1/378* (2006.01)
(52) U.S. Cl.
  CPC ........ *A61N 1/36067* (2013.01); *A61N 1/3787* (2013.01)
(58) Field of Classification Search
  USPC ........................................................ 320/108
  See application file for complete search history.

(56) References Cited

OTHER PUBLICATIONS

Bui Xuan Khuyen, Bui Son Tung, Young Joon Yoo, Young Ju Kim, Ki Won Kim, Liang-Yao Chen, Vu Dinh Lam, Young Pak Lee, Miniaturization for Ultrathin Metamaterial Perfect Absorber in the VHF Band; Scientific Reports, 7:45151, DOI: 10.1038/srep45151, pp. 1-7.

J. Choi and C. Seo; High-Efficiency Wireless Energy Transmission Using Magnetic Resonance Based on Metamaterial with Relative Permeability Equal to—1; Progress in Electromagnetics Research, vol. 106, pp. 33-47, 2010.

Ajit Rajagopalan, Anil Kumar Ramrakhyani, David Schurig, Gianluca Lazzi, Improving Power Transfer Efficiency of a Short-Range Telemetry System Using Compact Metamaterials; IEEE Transactions on Microwave Theory and Techniques; 0018-9480, 2014, pp. 1-9 (Digital Object Identifier: 10.1109/TMTT.2014.2304927).

Filiberto Bilotti, Alessandro Toscano, Lucio Vegni; Design of Spiral and Multiple Split-Ring Resonators for the Realization of Miniaturized Metamaterial Samples; IEEE Transactions on Antennas and Propagation, vol. 55, No. 8, Aug. 2007, pp. 2258-2267.

* cited by examiner

WIRELESS CHARGING DEVICE

This application claims priority for Taiwan patent application no. 107147273 filed on Dec. 26, 2018, the content of which is incorporated by reference in its entirely.

BACKGROUND OF THE INVENTION

Field of the Invention

The present invention relates to wireless technology for supplying power, particularly to a wireless charging device for charging a device installed within a human body.

Description of the Related Art

Parkinson's disease (PD) is a chronic neurodegenerative disease affecting the central nervous system. Parkinson's disease mainly affects the motor nervous system, such that patients are prone to tremors, limb stiffness, motor dysfunction, etc.

In order to alleviate the symptoms of Parkinson's disease, a part of treatment will implant a brain pacemaker into the patient's chest and connects a wire to the specific location of the patient's brain. When the brain of a patient with Parkinson's disease produces an abnormal electrical signal, the brain pacemaker implanted in the chest will produce a reversed electrical signal, which will then reach the brain via the wire, thereby causing the electrode of the wire to stimulate the subthalamic nucleus and to reduce the involuntary jitter of the patient's limbs However, when the brain pacemaker is charged, the wireless charger must be placed at one side of a shawl, and then the user wears the shawl for charging. Simultaneously, counterweights are placed at the other side of the shawl, such that the wireless charger accurately aligns to the brain pacemaker. Nevertheless, the charging electromagnetic wave transmitted by the wireless charger is quite unstable at present. When the wireless charger is deflected with respect to the brain pacemaker, or the distance between them is slightly farther, the charging efficiency is easily lowered, and the charging time is lengthened. In addition, it is possible to make the brain rhythm completely uncharged, thereby causing waste of time and confusion of users.

To overcome the abovementioned problems, the present invention provides a wireless charging device, so as to solve the afore-mentioned problems of the prior art.

SUMMARY OF THE INVENTION

The primary objective of the present invention is to provide a wireless charging device, which increases the intensity of a charging signal to avoid the low charging efficiency caused by deflection and too long a distance.

Another objective of the present invention is to provide a wireless charging device, which has a simple structure and components with low cost. The present invention not only effectively reduces the cost, but also increases the production efficiency due to the simple structure.

To achieve the abovementioned objectives, the present invention provides a wireless charging device, which comprises a wireless charging transmitter and at least one signal gain module. The signal gain module comprises an insulation substrate, a first conductive wire, a second conductive wire, and a connecting element. The wireless charging transmitter, provided with a transmitting terminal, uses the transmitting terminal to emit at least one charging signal. The signal gain module, arranged at the transmitting terminal of the wireless charging transmitter, receives the at least one charging signal and generates at least one gain signal. The insulation substrate has an upper surface and a lower surface, the center of the upper surface is provided with a first buffer portion, and the center of the lower surface is provided with a second buffer portion. The first conductive wire, arranged on the upper surface of the insulation substrate, outwardly makes at least one turns around the first buffer portion. The second conductive wire whose position corresponds to the position of the first conductive wire, arranged on the lower surface of the insulation substrate, outwardly makes at least one turns around the second buffer portion. The connecting element electrically connected to the first conductive wire and the second conductive wire, and the first conductive wire is electrically connected to the second conductive wire through the connecting element.

In an embodiment of the present invention, the wireless charging device further comprises a casing encasing the wireless charging transmitter and the signal gain module, and the signal gain module is emerged from the surface of the casing.

In an embodiment of the present invention, each of the first buffer portion and the second buffer portion has a width of at least 5 cm.

In an embodiment of the present invention, the first conductive wire further outwardly making at least two turns around the first buffer portion, and the at least two turns of the first conductive wire are spaced from each other, and the second conductive wire further outwardly making at least two turns around the second buffer portion, and the at least two turns of the second conductive wire are spaced from each other, wherein a gap between neighboring two of the at least two turns of the first conductive wire has a distance of 0.5~3 mm, and a gap between neighboring two of the at least two turns of the second conductive wire has a distance of 0.5~3 mm. The width of each of the first conductive wire and the second conductive wire has a width of at least 1 mm.

Below, the embodiments are described in detail in cooperation with the drawings to make easily understood the technical contents, characteristics and accomplishments of the present invention.

DETAILED DESCRIPTION OF THE INVENTION

The present invention discloses a wireless charging device with high charging efficiency, which provides a charging signal with high intensity to avoid the low charging efficiency caused by deflection and too long a distance.

Figure 1:
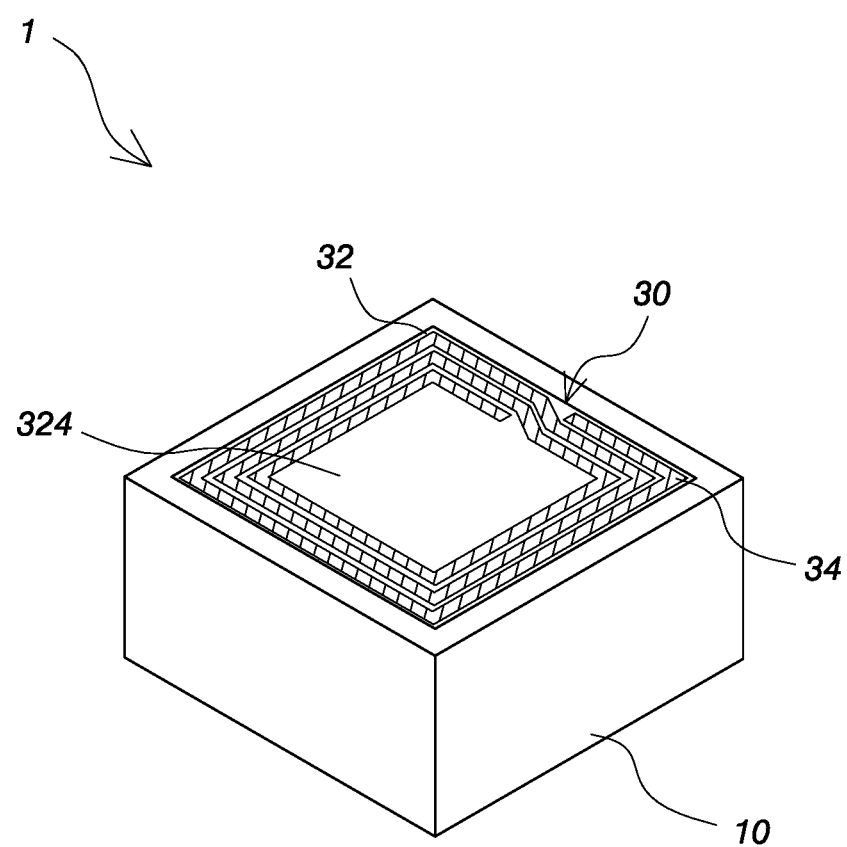
FIG. 1 is a perspective view of a wireless charging device according to an embodiment of the present invention.
Figure 2:
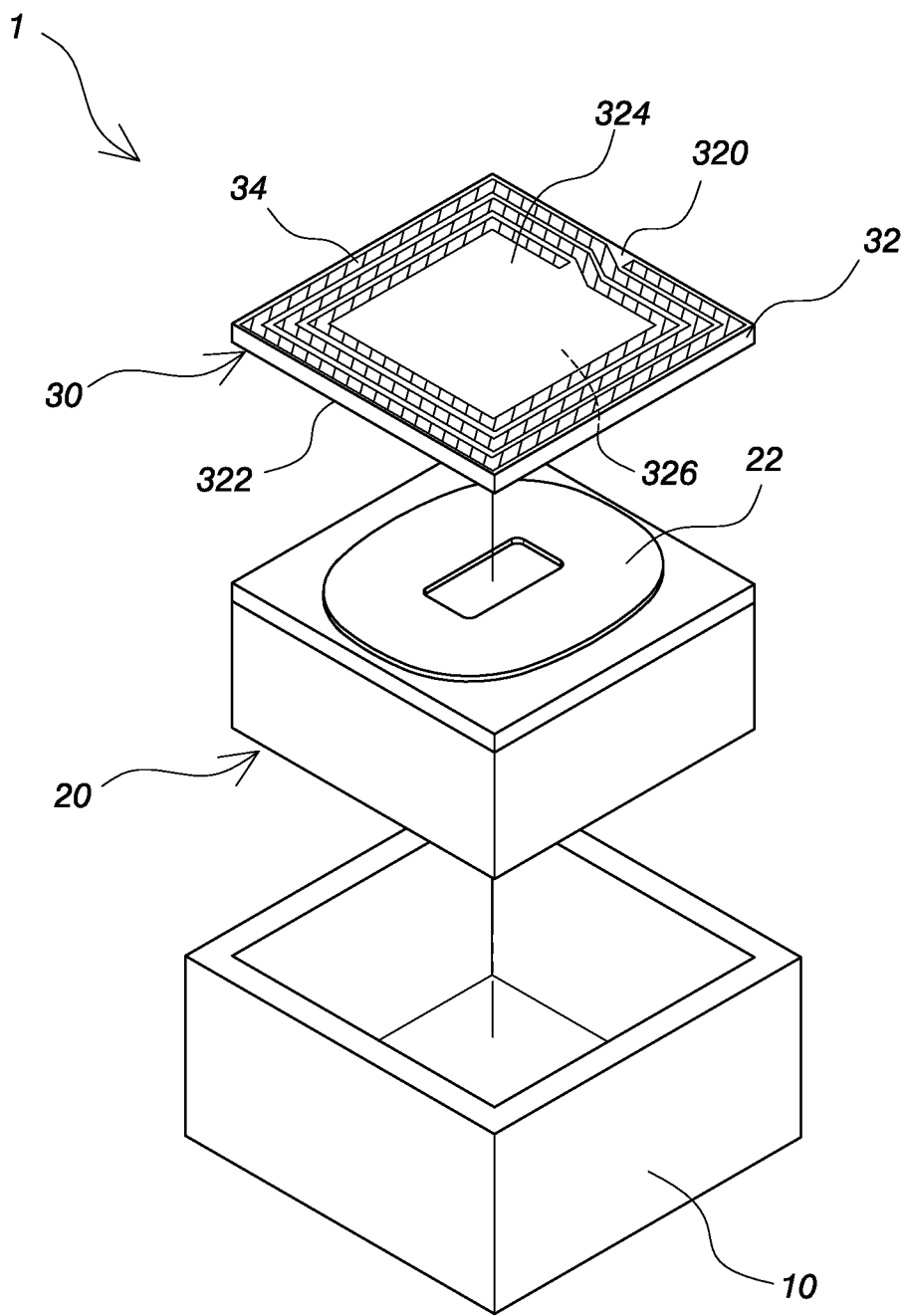
FIG. 2 is an exploded view of a wireless charging device according to an embodiment of the present invention.

The structure of the wireless charging device of the present invention is described as follows. Refer to FIG. 1 and FIG. 2. The wireless charging device 1 comprises a casing 10 encasing a wireless charging transmitter 20 and at least one signal gain module 30. The signal gain module 30 is emerged from the surface of the casing 10. The wireless charging transmitter 20 is provided with a transmitting terminal 22. The wireless charging transmitter 20 uses the transmitting terminal 22 to emit at least one charging signal. The signal gain module 30 is arranged on the casing 10 and arranged at the transmitting terminal 22 of the wireless charging transmitter 20. The signal gain module 30 receives the charging signal and generates at least one gain signal, such that an external receiving device to be charged (not shown) receives the gain signal. The receiving device is charged according to the gain signal.

Figure 3:
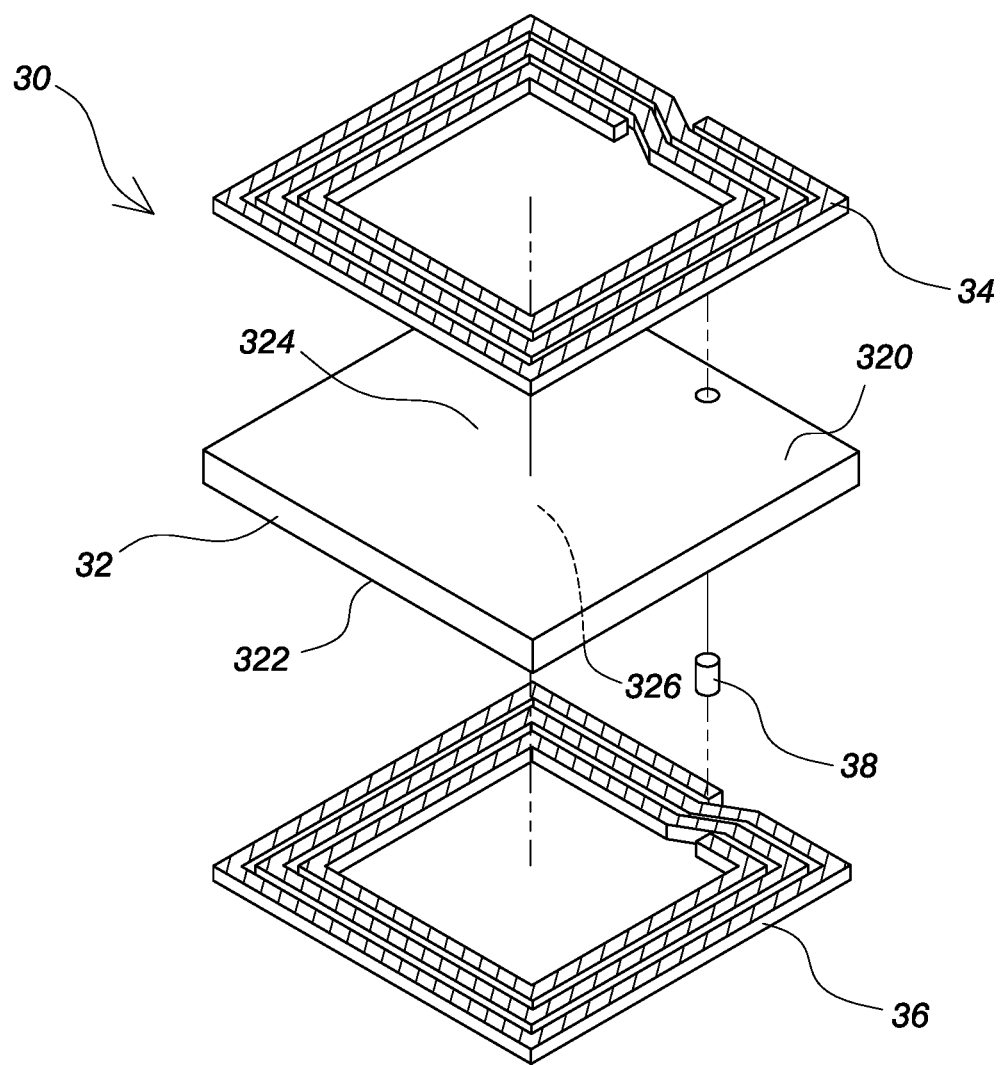
FIG. 3 is an exploded view of signal gain module according to an embodiment of the present invention.
Figure 4:
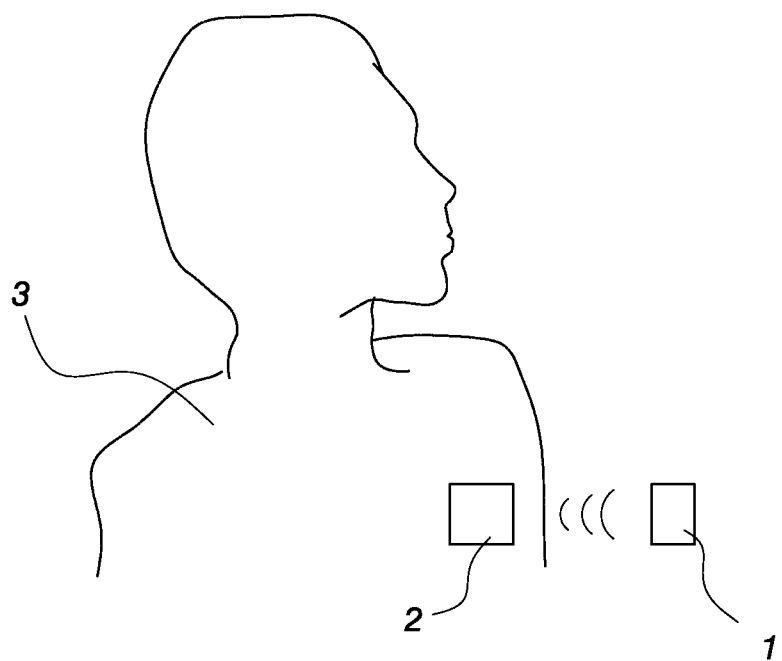
FIG. 4 is a diagram schematically showing a state of using a wireless charging device according to an embodiment of the present invention.
Figure 5:
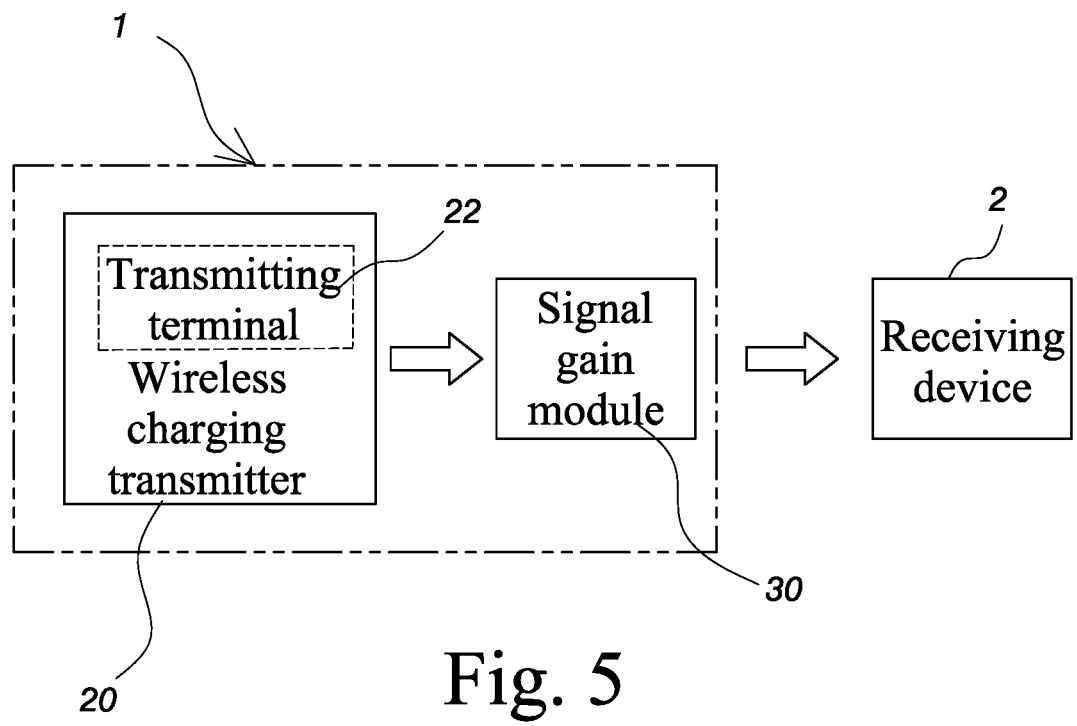
FIG. 5 is a diagram schematically showing a wireless charging device and a charging receiving device according to an embodiment of the present invention.

Refer to FIG. 1, FIG. 2, and FIG. 3. The structure of the signal gain module 30 is detailed as follows. The signal gain module 30 of the embodiment comprises an insulation substrate 32. The insulation substrate 32 may be a printed circuit board (PCB), a glass substrate or a silicon substrate. The insulation substrate 32 includes an upper surface 320 and a lower surface 322. The center of the upper surface 320 is provided with a first buffer portion 324. The center of the lower surface 322 is provided with a second buffer portion 326.

Refer to FIG. 3. The upper surface 320 of the insulation substrate 32 is provided with a first conductive wire 34. The first conductive wire 34 may comprise copper, composite metal or metal. The first conductive wire 34 outwardly makes at least one turns around the first buffer portion 324, but in an embodiment of the present invention, the first conductive wire 34 outwardly makes at least three turns around the first buffer portion 324. The first conductive wire 34 is spirally arranged on the insulation substrate 32. There is a gap between neighboring two of at least three turns of the first conductive wire 34. In the embodiment, the first buffer portion 324 has a width of at least 5 cm, the first conductive wire 34 has a width of at least 1 mm, and the gap between neighboring two of the at least three turns of the first conductive wire 34 has a distance of 0.5-3 mm. The design can avoid interference among signals. The lower surface 322 of the insulation substrate 32 is provided with a second conductive wire 36. The second conductive wire 36 may comprise copper, composite metal or metal. One end of the first conductive wire 34 and one end of the second conductive wire 36 are connected to a connecting element 38. The connecting element 38 may be a copper post. The first conductive wire 34 is electrically connected to the second conductive wire 36 through the copper post. The second conductive wire 36 whose position corresponds to the position of the first conductive wire 34 is arranged on the lower surface 322 of the insulation substrate 32. The second conductive wire 36 outwardly makes at least one turns around the second buffer portion 326, but in an embodiment of the present invention, the second conductive wire 34 outwardly makes at least three turns around the second buffer portion 324. The second conductive wire 36 is spirally arranged on the insulation substrate 32. The at least three turns of the second conductive wire 36 are spaced from each other. In the embodiment, the direction of winding the second conductive wire 36 is contrary to the direction of winding the first conductive wire 34. Thus, when the signal is transmitted from the first conductive wire 34 to the second conductive wire 36, the direction of transmitting the signal is maintained. That is to say, the signal is not affected by the direction of winding the first conductive wire 34 and the second conductive wire 36. In addition, the gap between neighboring two of the at least three turns of the second conductive wire 36 and the width of the second conductive wire 36 are respectively the same to the gap between neighboring two of the at least three turns of the first conductive wire 34 and the width of the first conductive wire 34. In the embodiment, the second buffer portion 326 has a width of at least 5 cm, the second conductive wire 36 has a width of at least 1 mm, and the gap between neighboring two of the at least three turns of the second conductive wire 36 has a distance of 0.5-3 mm. The design can avoid interference among signals.

After describing the structure of the wireless charging device 1, the state of using a wireless charging device 1 is introduced as follows. Refer to FIG. 1, FIG. 2, FIG. 3, FIG. 4, and FIG. 5. In the embodiment, the wireless charging device 1 charges the receiving device 2 to be charged within a human body 3. The receiving device 2 to be charged may be a brain rhythm. When the receiving device 2 is charged, a user locates the wireless charging device 1 in a position close to the receiving device 2 and drives the transmitting terminal 22 of the wireless charging transmitter 20 to emit a charging signal. The signal gain module 30 receives the charging signal to generate a gain signal, which is provided to the receiving device 2 for charging. As a result, the present invention uses the signal gain module 30 to effectively enhance the intensity of the charging signal. In other words, the transmitting terminal 22 of the wireless charging transmitter 20 of the wireless charging device 1 effectively charges the receiving device 2 without horizontally aiming at the receiving terminal of the receiving device 2 when the wireless charging device 1 charges the receiving device 2 within the human body 3.

Figure 6A:
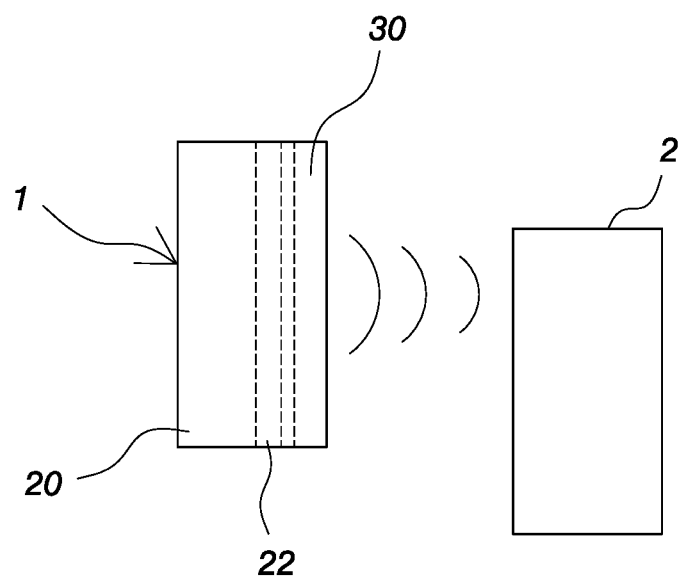
FIG. 6a is a diagram schematically showing a wireless charging device and a dislocated charging receiving device according to an embodiment of the present invention.
Figure 6B:
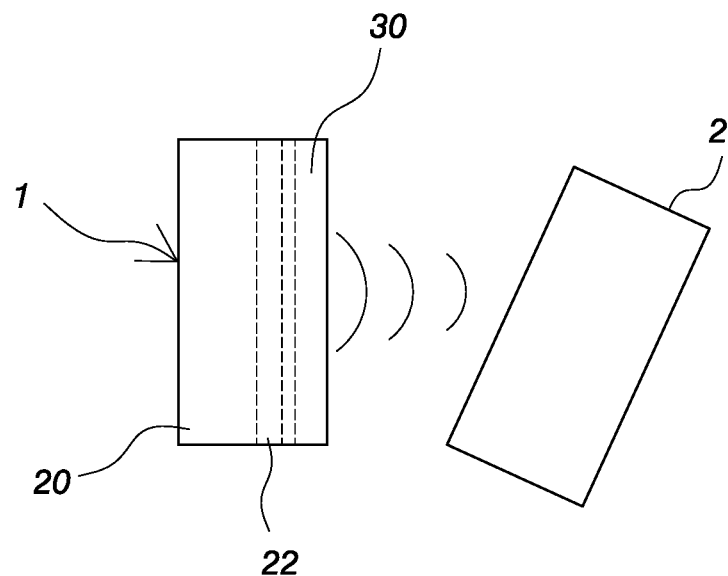
FIG. 6b is a diagram schematically showing a wireless charging device and a deflected charging receiving device according to an embodiment of the present invention.

Refer to FIG. 6a. The receiving device 2 still receives the 51% charging signal when the transmitting terminal 22 of the wireless charging transmitter 20 of the wireless charging device 1 is deflected with respect to the receiving device 2 within the human body or when the distance between the transmitting terminal 22 of the wireless charging transmitter 20 of the wireless charging device 1 and the receiving device 2 is too long. In the past, the conventional wireless charger transmits a 46% charging signal to the receiving device to be charged when the conventional wireless charger is deflected with respect to the receiving device or when the distance between the conventional wireless charger and the receiving device is too long. Compared with the conventional technology, the wireless charging device 1 of the present invention can achieve the better charging efficiency. Refer to FIG. 6b. The receiving device 2 still receives the 46% charging signal when the transmitting terminal 22 of the wireless charging transmitter 20 of the wireless charging device 1 is deflected with respect to the receiving device 2 within the human body. In the past, the conventional wireless charger transmits a 39% charging signal to the receiving device to be charged when the conventional wireless charger is deflected with respect to the receiving device. Compared with the conventional technology, the wireless charging device 1 of the present invention can achieve the better charging efficiency. As a result, the wireless charging device 1 of the present invention can avoid horizontally aiming the transmitting terminal of the wireless charging device at the receiving terminal of the receiving device to be charged during a charging process and causing inconvenience of the user.

Figure 7:
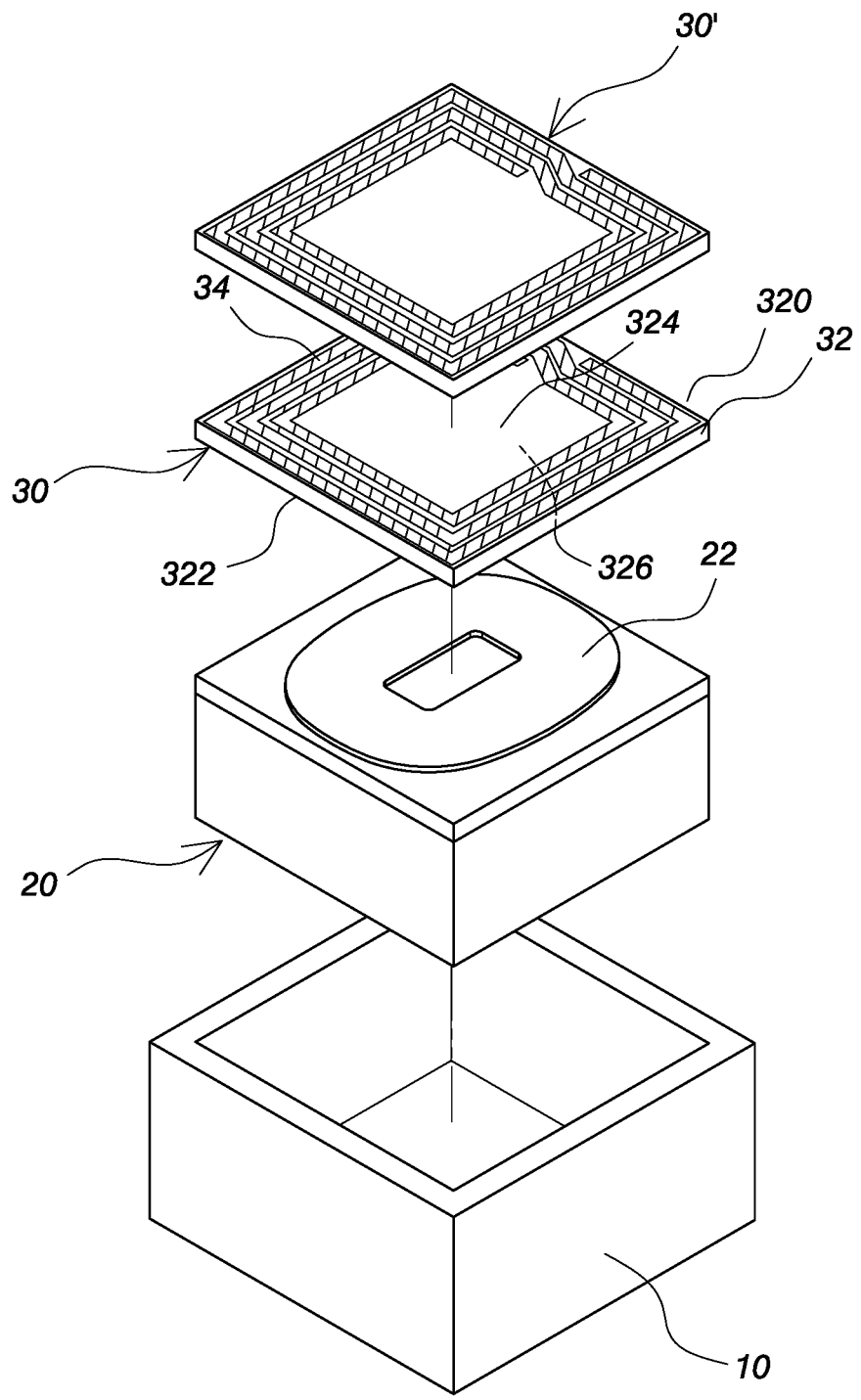
FIG. 7 is a perspective view of a wireless charging device according to another embodiment of the present invention.

Refer to FIG. 7. FIG. 7 is a perspective view of a wireless charging device according to another embodiment of the present invention. Like the abovementioned embodiment, the wireless charging device 1 comprises a casing 10 encasing a wireless charging transmitter 20. The structures and the states of using the casing 10 and the wireless charging transmitter 20 are the same to those of the previous embodiment so will not be reiterated. The embodiment is different from the previous embodiment in that the casing 10 is provided with two signal gain modules 30 and 30' therein. In the embodiment, the distance between the signal gain modules 30 and 30' is maintained at least 0.5 cm. The signal gain modules 30 and 30' are arranged at the transmitting terminal 22 of the wireless charging transmitter 20. The signal gain modules 30 and 30' receive the charging signal to generate at least one gain signal and transmit the gain signal to an external receiving device to be charged (not shown). The structures and the states of using the signal gain module 30' are the same to those of the previous embodiment so will not be reiterated.

In conclusion, the present invention provides a charging signal with high intensity to avoid the low charging efficiency caused by deflection and too long a distance. The present invention has a simple structure and components with low cost. The present invention not only effectively reduces the cost, but also increases the production efficiency due to the simple structure.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:
1. A wireless charging device comprising:
   a wireless charging transmitter, provided with a transmitting terminal, using the transmitting terminal to emit at least one charging signal; and
   at least one signal gain module, arranged at the transmitting terminal of the wireless charging transmitter, receiving the at least one charging signal and generating at least one gain signal, and the at least one signal gain module comprises:
     an insulation substrate having an upper surface and a lower surface, a center of the upper surface is provided with a first buffer portion, and a center of the lower surface is provided with a second buffer portion;
     a first conductive wire, arranged on the upper surface of the insulation substrate, outwardly making at least one turns around the first buffer portion;
     a second conductive wire whose position corresponds to a position of the first conductive wire, arranged on the lower surface of the insulation substrate, outwardly making at least one turns around the second buffer portion; and
     a connecting element electrically connected to the first conductive wire and the second conductive wire, and the first conductive wire is electrically connected to the second conductive wire through the connecting element.

2. The wireless charging device according to claim 1, further comprising a casing encasing the wireless charging transmitter and the signal gain module, and the signal gain module is emerged from a surface of the casing.

3. The wireless charging device according to claim 1, wherein the first conductive wire and the second conductive wire are spirally arranged on the insulation substrate.

4. The wireless charging device according to claim 1, wherein the connecting element is electrically connected to an end of the first conductive wire and an end of the second conductive wire.

5. The wireless charging device according to claim 1, wherein the connecting element is a copper post.

6. The wireless charging device according to claim 1, wherein each of the first buffer portion and the second buffer portion has a width of at least 5 cm.

7. The wireless charging device according to claim 1, wherein the first conductive wire further outwardly making at least two turns around the first buffer portion, and the at least two turns of the first conductive wire are spaced from each other, and the second conductive wire further outwardly making at least two turns around the second buffer portion, and the at least two turns of the second conductive wire are spaced from each other, wherein a gap between neighboring two of the at least two turns of the first conductive wire has a distance of 0.5~3 mm, and a gap between neighboring two of the at least two turns of the second conductive wire has a distance of 0.5~3 mm.

8. The wireless charging device according to claim 1, wherein a width of each of the first conductive wire and the second conductive wire has a width of at least 1 mm.

9. The wireless charging device according to claim 1, wherein the first conductive wire and the second conductive wire comprise copper, composite metal or metal.

10. The wireless charging device according to claim 1, wherein the insulation substrate is a printed circuit board (PCB), a glass substrate or a silicon substrate.

* * * * *